United States Patent
Nakanishi et al.

(10) Patent No.: US 7,795,474 B2
(45) Date of Patent: Sep. 14, 2010

(54) 6,8,10-UNDECATRIEN-3-ONE OR 6,8,10-UNDECATRIEN-4-ONE, AND AROMA COMPOSITIONS

(75) Inventors: Akira Nakanishi, Tokyo (JP); Yasutaka Ohkubo, Yokohama (JP); Naomi Tomita, Kawasaki (JP); Norio Miyazawa, Tokyo (JP); Tomoko Maeda, Tokyo (JP)

(73) Assignee: T. Hasegawa Co., Ltd., Tokyo (JP)

( * ) Notice: Subject to any disclaimer, the term of this patent is extended or adjusted under 35 U.S.C. 154(b) by 0 days.

(21) Appl. No.: 12/452,071

(22) PCT Filed: Apr. 3, 2008

(86) PCT No.: PCT/JP2008/057043

§ 371 (c)(1),
(2), (4) Date: Dec. 15, 2009

(87) PCT Pub. No.: WO2008/152858

PCT Pub. Date: Dec. 18, 2008

(65) Prior Publication Data

US 2010/0137648 A1 Jun. 3, 2010

(30) Foreign Application Priority Data

Jun. 15, 2007 (JP) ............................. 2007-158952
Sep. 28, 2007 (JP) ............................. 2007-254728
Sep. 28, 2007 (JP) ............................. 2007-254745

(51) Int. Cl.
*C07C 49/203* (2006.01)
*C07C 45/59* (2006.01)
*C07C 45/61* (2006.01)
*A61K 8/18* (2006.01)

(52) U.S. Cl. ........................ 568/386; 568/393; 568/417; 512/27

(58) Field of Classification Search ............... 568/386, 568/393, 417
See application file for complete search history.

(56) References Cited

U.S. PATENT DOCUMENTS

| 3,960,977 A | 6/1976 | Naf et al. |
| 4,014,951 A | 3/1977 | Naf et al. |

FOREIGN PATENT DOCUMENTS

| EP | 0 100 015 | 2/1984 |
| JP | 50-32105 | 3/1975 |
| JP | 59-42326 | 3/1984 |
| JP | 60-190730 | 9/1985 |
| JP | 61-91149 | 5/1986 |
| JP | 5-70394 | 3/1993 |
| JP | 8-92150 | 4/1996 |
| JP | 4057638 | 12/2007 |
| JP | 4057639 | 12/2007 |
| JP | 4057640 | 12/2007 |

OTHER PUBLICATIONS

Shuchi Kangyo Gijutsu-Shu, (Collection of Known Common Techniques), Aroma, Part III, "Aroma for Perfumed Cosmetics", pp. 32-33, Jun. 15, 2001, with partial English translation.
International Search Report issued Jun. 3, 2008 in International (PCT) Application No. PCT/JP2008/057043.

*Primary Examiner*—Sikarl A Witherspoon
(74) *Attorney, Agent, or Firm*—Wenderoth, Lind & Ponack, L.L.P.

(57) ABSTRACT

This invention offers 6,8,10-undecatrien-3-one or 6,8,10-undecatrien-4-one which are represented by the following formula (1)

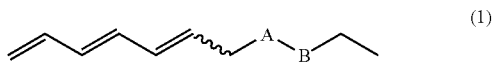

[in the formula, either one of A and B stands for carbonyl group and the other stands for methylene group, and the wavy line signifies cis-form, trans-form, or a mixture of cis- and trans-form at an optional ratio]
and which can reproduce an odor rich in naturality and freshness.

6 Claims, No Drawings

6,8,10-UNDECATRIEN-3-ONE OR 6,8,10-UNDECATRIEN-4-ONE, AND AROMA COMPOSITIONS

This application is a U.S. national stage of International Application No. PCT/JP2008/057043 filed Apr. 3, 2008.

TECHNICAL FIELD

This invention relates to 6,8,10-undecatrien-3-one or 6,8,10-undecatrien-4-one which are novel compounds useful as aroma compounds, to novel aroma compositions containing those compounds as the active ingredient, and to methods for preparation of the compounds.

BACKGROUND ART

Heretofore many reports have been made on aroma components of galbanum essential oil, and its characteristic aroma is of interest. Galbanum essential oil has fresh green note basically of balsamic bark odor accompanied by dry woody note, and holds an important place mainly in fragrance utility as a natural green note material.

Main arom a components of galbanum essential oil are hydrocarbons including β-pinene, $\Delta^3$-carene, α-pinene, d-limonene and 1,3,5-undecatriene, and as other components, pyrazines, thiocarboxylic acids and esters are known. Also as the characteristic components of galbanum absolute, 12-tridecanolide, 13-tetradecanolide, 14-pentadecanolide and the like have been found (cf. Shuchi Kanyo Gijutsu-Shu (collection of known common techniques), Aroma, Part III, "Aroma for perfumed cosmetics", p. 32-33).

DISCLOSURE OF THE INVENTION

In recent years, consumers' tastes are diversified, and materials rich in naturality and freshness are in demand, as aromas for food and beverage, perfumed cosmetics and the like. At the present time, however, such demands cannot be fully met by simply combining conventional aroma substances.

The object of the present invention is to offer novel aroma compounds which can reproduce an odor rich in naturality and freshness, and methods of their preparation.

We noticed the possible presence of novel aroma components contributing to the fresh green note of galbanum essential oil, other than above known components, and searched for the novel trace aroma components. In consequence, we discovered the existence in galbanum essential oil of 6,8,10-undecatrien-3-one or 6,8,10-undecatrien-4-one which are novel substances not disclosed in literature, and succeeded in their chemical synthesis. We furthermore discovered that the compounds have green note with dry woody tone and, still in addition, sweet, fruity note and taste rich in naturality and freshness. This invention is whereupon completed.

Thus, the present invention offers 6,8,10-undecatrien-3-one or 6,8,10-undecatrien-4-one, which are represented by the following formula (1):

(1)

[in the formula, either one of A and B is carbonyl group and the other is methylene group, the wavy line signifying cis-form, trans-form or a mixture of cis- and trans-forms at an optional ratio].

This invention also offers aroma compositions which are characterized by containing 6,8,10-undecatrien-3- or -4-one of the formula (1) as the active ingredient.

The compounds of the formula (1) of the present invention possess, in addition to the green note with dry woody tone, sweet fruity note and taste rich in naturality and freshness with excellent lasting effect, and are useful as constituent materials of aroma compositions for food and beverage, perfumed cosmetics; health and sanitation goods and medicaments.

Hereinafter the compounds of the invention, methods of their preparation and their utility for aroma compositions are explained in further details.

DETAILED DESCRIPTION OF THE INVENTION

While 6,8,10-undecatrien-3- or -4-one of the formula (1), the compounds of the present invention, can be extracted and isolated from galbanum essential oil, the compound of the formula (1) in which A is methylene group and B is carbonyl group, i.e., the compound of the following formula (1-1),

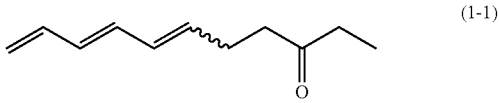

(1-1)

can be chemically synthesized, for example, by subjecting a phosphonium salt of the following formula (2),

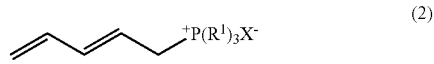

(2)

[in the formula, $R^1$ stands for an aryl and X stands for a halogen]

or a phosphonate of the following formula (3),

(3)

[in the formula, $R^2$ stands for a $C_{1-8}$ alkyl or aryl]

to Wittig reaction or Horner-Emmons reaction, with a lactol of the following formula (4)

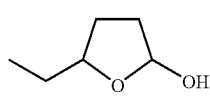

(4)

and oxidizing the resulting 6,8,10-undecatrien-3-ol which is represented by the following formula (5)

(5)

[in the formula, the wavy line signifies cis-form, trans-form or a mixture of cis- and trans-forms at an optional ratio];

or by subjecting the phosphonium salt of above formula (2) or to phosphonate of the formula (3) to Wittig reaction or Horner-Emmons reaction with a ketoaldehyde of the following formula (6)

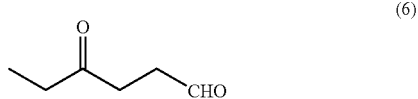

(6)

following the reaction scheme 1 or 2 below:

Reaction Scheme 1

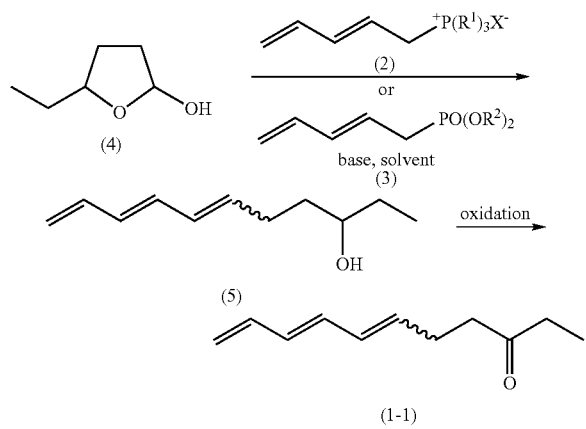

[in the formulae, the wavy line, $R^1$, X and $R^2$ have the previously defined significations].

Reaction Scheme 2

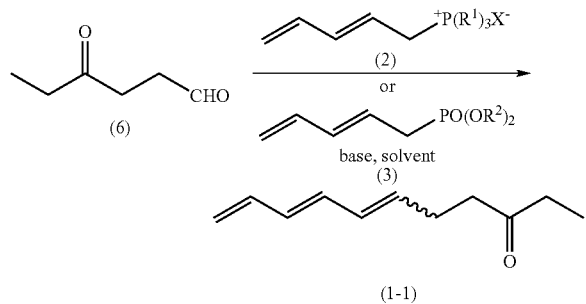

[in the formula, the wavy line, $R^1$, X and $R^2$ have the previously defined significations].

In the present specification, "aryl" includes monocyclic or polycyclic aromatic hydrocarbon groups, for example, optionally substituted phenyl, tolyl, naphthyl and the like, preferably phenyl.

"Alkyl" is a straight chain or branched chain saturated hydrocarbon group, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or the like. Of those, $C_{1-6}$ lower alkyl groups are preferred.

"Halogen atom" includes fluorine, chlorine, bromine and iodine atoms, and particularly preferred halogen as X is chlorine or bromine.

The Wittig reaction of a phosphonium salt of the formula (2) with a lactol of the formula (4) or ketoaldehyde of the formula (6), or the Horner-Emmons reaction of a phosphonate of the formula (3) with a lactol of the formula (4) or ketoaldehyde of the formula (6) can be performed under the typical conditions for these reactions as described in the literature (e.g., see Shin-jikkenkagaku Koza (lectures on new experimental chemistry) 14, Syntheses and reactions of organic compounds [I], p. 224-243).

The Wittig reaction of a phosphonium salt of the formula (2) with a lactol of the formula (4) or ketoaldehyde of the formula (6) is usually performed in an inert organic solvent in the presence of a base. Examples of the organic solvent useful in that occasion include ether (e.g., diethyl ether, diisopropyl ether, methyl t-butyl ether, 1,4-dioxane, tetrahydrofuran and the like); halogenated hydrocarbon (e.g., dichloromethane, chloroform and the like); aromatic hydrocarbon (e.g., benzene, toluene, xylene and the like); and polar solvent (e.g., dimethylformamide, dimethylsulfoxide, acetonitrile and the like). In particular, toluene, tetrahydrofuran, dimethylsulfoxide, dimethylformamide or mixtures thereof are preferred.

As the base, any of the bases usually used in Wittig reaction can be used, examples of which include alkali metal hydroxide (e.g., sodium hydroxide, potassium hydroxide, lithium hydroxide and the like); alkali metal hydride (e.g., sodium hydride, potassium hydride and the like); organolithium compound (e.g., n-butyllithium, t-butyllithium, phenyllithium and the like); alkali metal amide (e.g., lithium amide, potassium amide, sodium amide, lithium diisopropylamide and the like); alkali metal hexamethyldisilazide; and alkali metal alcoholate (e.g., sodium methoxide, sodium ethoxide and the like). The use rate of these bases is normally within a range of 0.8-5 equivalent, preferably 1-3 equivalent, per mol of the phosphonium salt of the formula (2).

Also the use rate of the lactol of the formula (4) or ketoaldehyde of the formula (6) per mol of the phosphonium salt of the formula (2) can normally be within a range of 0.8-5 mol, preferably 1-3 mol.

The Wittig reaction can be performed normally at temperatures within a range of −78 to 60° C., preferably from −10 to 25° C., normally for about 0.5-24 hours, preferably about 0.5-2 hours.

The Horner-Emmons reaction of a phosphonate of the formula (3) with a lactol of the formula (4) or ketoaldehyde of the formula (6) can be performed in the manner similar to the Wittig reaction of a phosphonium salt of the formula (2) with a lactol of the formula (4) or ketoaldehyde of the formula (6).

Thus, depending on the reaction conditions adopted, 6,8,10-undecatrien-3-ol of the formula (5) or 6,8,10-undecatrien-3-one of the formula (1-1) can be obtained in the form of a mixture of the geometrical isomers, in which the cis-form: trans-form ratio at the wavy line in the formula (5) or (1-1) lies within a range of generally 10:1-1:10, in particular 7:3-3:7.

Oxidation of so obtained 6,8,10-undecatrien-3-ol of the formula (5) to form 6,8-10-undecatrien-3-one of the formula (1-1) can be performed under the conditions known per se for converting secondary alcohol to ketone. More specifically, the oxidation can be performed by the methods as described in literature (e.g., see Shin-jikkenkagaku Koza, 15, "Oxidation and Reduction" [I-1], p. 108-123), such as oxidation with chromium (VI) oxide-dilute sulfuric acid, Jones oxidation, oxidation with chromium (VI) oxide-pyridine complex (Sarret oxidation, Collins oxidation), pyridinium chlorochromate (PCC) oxidation and pyridinium dichromate (PDC) oxidation; Oppenauer oxidation as described in literature (e.g., see Shin-jikkenkagaku Koza 15, "Oxidation and Reduction" [I-2], p. 870-873; Dess-Martin oxidation as described in literature (e.g., see J. Org. Chem., 48 (1983) 4155); oxidation with o-iodoxybenzoic acid (IBX) as described in literature (e.g., see J. Am. Chem. Soc., 122 (2000), 7596); or oxidation with tetrapropylammonium perruthenate (TPAP) as described in literature (e.g., see Synthesis, (1994), 639). Dess-Martin oxidation and oxidation with IBX or TPAP are particularly preferred.

Lactol of the formula (4) which is used as a starting material can be synthesized, for example, according to the following reaction scheme 3 (see Shin-jikkenkagaku Koza 15, "Oxidation and Reduction" [II], p. 98).

Reaction Scheme 3

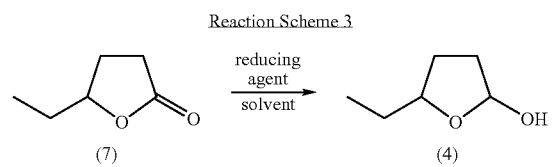

Lactol of the formula (4) can be obtained by reacting readily available γ-hexylactone of the formula (7) with a reducing agent such as, for example, diisobutylaluminum hydride (DIBAL), in an inert gaseous atmosphere, in an inert organic solvent such as toluene, hexane and the like.

Ketoaldehyde of the formula (6) which is also used as a starting material is a known compound and can be synthesized, for example, according to the following reaction scheme 4 (see Helvetica Chimica Acta, Vol. 61, Fasc. 3 (1978), 990-997).

Reaction Scheme 4

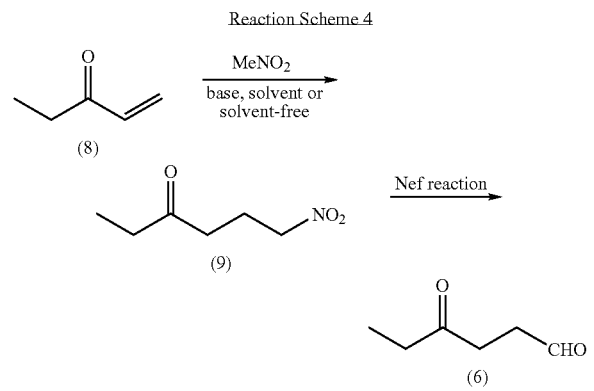

Ketoaldehyde of the formula (6) can be obtained by subjecting nitromethane to Michael addition reaction to readily available ethyl vinyl ketone of the formula (8), for example, in the presence of a base such as sodium methoxide, in an organic solvent such as methanol or under solvent-free condition, and then subjecting the resulting nitro compound of the formula (9) to Nef reaction. The Nef reaction can be performed under the conventional conditions as described in literature (e.g., see Yuki Jinmei Hanno (Named Organic Reaction), p. 109-110).

The phosphonium salt of the formula (2) or the phosphonate of the formula (3) to be reacted with lactol of the formula (4) or ketoaldehyde of the formula (6) are known compounds which can be synthesized following the method disclosed in literature (e.g., see JP 50(1975)-32105A), for example, as illustrated in the reaction scheme 5.

Reaction Scheme 5

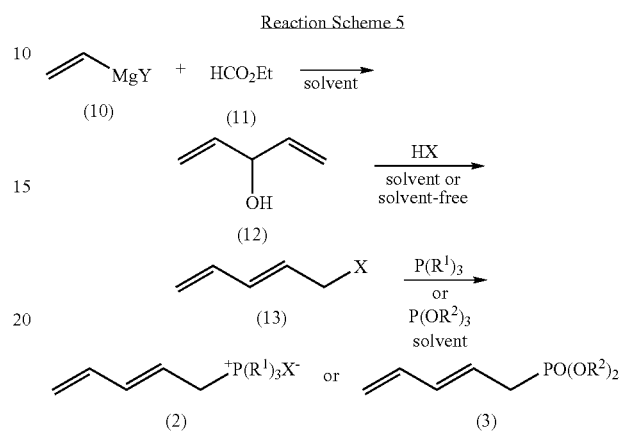

[in the formula, Y stands for halogen, and $R^1$, X and $R^2$ have the earlier given significations]

A Grignard reagent of the formula (10) which is a starting material can be prepared from vinyl halide and magnesium metal according to a conventional method. As the vinyl halide, vinyl chloride and vinyl bromide are preferred. The alcohol of the formula (12) can be obtained by reacting at least 2 equivalent of the Grignard reagent of the formula (10) per mol of ethyl formate of the formula (11) in a solvent such as diethyl ether, tetrahydrofuran or the like.

The alcohol of the formula (12) can be similarly obtained when ethyl formate of the formula (11) in the above Grignard reaction is replaced with acrolein.

Then subjecting the alcohol of the formula (12) to a nucleophilic substitution with hydrogen halide (HX), the halide of the formula (13) can be obtained. As the hydrogen halide (HX), hydrogen chloride or hydrogen bromide are preferred, and this reaction can be carried out by adding, per mol of the alcohol of the formula (12), a 20-60% aqueous solution of 1-3 mol of hydrogen chloride or hydrogen bromide.

Successively reacting a mol of the halide of the formula (13) with 1-5 equivalent of phosphine [$P(R^1)_3$] or phosphite [$P(OR^2)_3$] by a conventional method, the phosphonium salt of the formula (2) or the phosphonate of the formula (3) can be obtained.

Also a compound of the formula (1) in which A is carbonyl group and B is methylene group, i.e., the compound of the following formula (1-2)

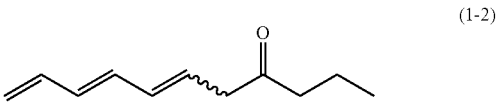

can be chemically synthesized, for example, according to the following reaction scheme 6, by subjecting a phosphonium salt of the formula (2) or phosphonate of the formula (3) to Wittig reaction or Horner-Emmons reaction with an aldehyde of the formula (14)

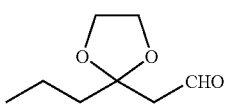

and deacetalizing the resulting trieneacetal of the formula (15)

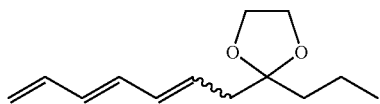

[in the formula, the wavy line has the earlier given signification].

Reaction Scheme 6

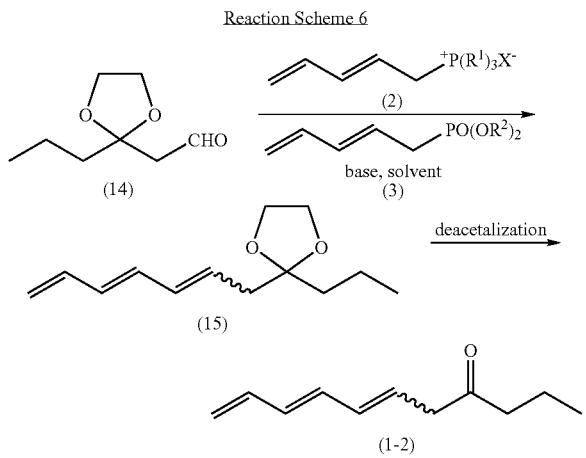

[in the formula, the wavy line, $R^1$, X and $R^2$ have the earlier given definitions].

The Wittig reaction of phosphonium salt of the formula (2) with aldehyde of the formula (14) or the Horner-Emmons reaction of phosphonate of the formula (3) with aldehyde of the formula (14) can be performed in the manner similar to the Wittig reaction of a phosphonium salt of the formula (2) with a lactol of the formula (4) or a ketoaldehyde of the formula (6), or the Horner-Emmons reaction of a phosphonate of the formula (3) with a lactol of the formula (4) or a ketoaldehyde of the formula (6) as earlier described.

Thus the trieneacetal of the formula (15) or 6,8,10-undecatrien-4-one of the formula (1-2) is obtained in the form of a mixture of geometrical isomers in which the cis-form: trans-form ratio at the wavy line in the formula (15) or (1-2) lies generally within a range of 10:1-1:10, in particular 7:3-3:7, depending on the reaction conditions adopted.

The reaction to produce 6,8,10-undecatrien-4-one of the formula (1-2) by deacetalization of trieneacetal of the formula (15) can be performed under conventional deacetalization conditions as described in literature (see, for example, Protective Groups in Organic Synthesis, Greene Wuts, p. 317-322). More specifically, it can be performed, for example, by an acetal exchange reaction using an acid catalyst (e.g., pyridinium p-toluenesulfonate (PPTS)-acetone-water, p-toluenesulfonic acid (TsOH)-acetone or the like); hydrolysis using an acid catalyst (e.g., hydrochloric acid-tetrahydrofuran, acetic acid, perchloric acid or the like); or oxidation (DDQ-acetonitrile-water or the like).

The aldehyde of the formula (14) which is used as the starting material can be synthesized, for example, according to the following reaction scheme 7.

Reaction Scheme 6

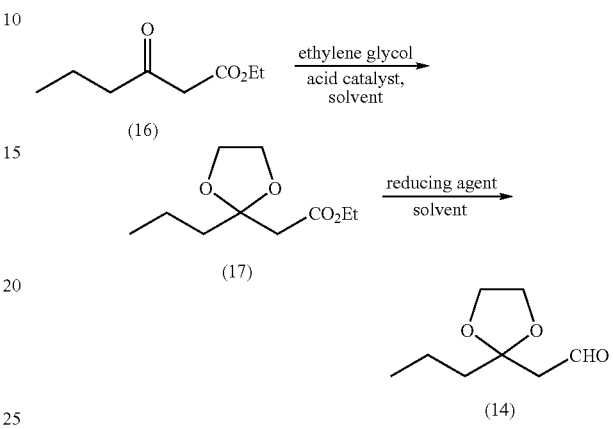

The compound of the formula (17) can be obtained by acetalization of readily available ethyl 3-oxohexanoate of the formula (16) with ethylene glycol. This acetalization can be performed under the typical conditions for this kind of reactions as described in literature (for example, see Protective Groups in Organic Synthesis, Greene Wuts, p. 312-316). More specifically, for example, by carrying out the reaction in an azeotropic solvent with water such as benzene, toluene, cyclohexane or the like, using an acid catalyst such as pyridinium p-toluenesulfonate (PPTS), p-toluenesulfonic acid (TsOH), camphorsulfonic acid (CSA) or the like, at the boiling point of the solvent while removing the formed water, the compound of the formula (17) can be produced.

Then the compound of the formula (17) is reduced in an inert gaseous atmosphere, using a reducing agent such as, for example, diisobutylaluminum hydride (DIBAL), in an inert organic solvent such as toluene, hexane or the like, to give the aldehyde of the formula (14).

The compounds of the formula (1) offered by the present invention possess, in addition to green note with dry woody tone, sweet fruity note and taste rich in naturality and freshness, and are capable of imparting fresh and very natural note to aroma compositions, when blended therewith at a specific ratio.

The compounds of the formula (1) have the fragrance and flavor characteristics as above, regardless of the bond form at the part indicated with the wavy line in the formula (1), which may be cis-form, trans-form or a mixture of cis- and trans-forms at an optional ratio. Accordingly, the compounds of the invention are useful in the aroma compositions, irrelevantly to the geometrical configuration of the part indicated with the wavy line.

When a compound of the formula (1) is blended with an aroma composition, its blend ratio differs depending on the purpose of blending, kind of the aroma composition and so on. Whereas, it can normally be within a range of 0.00001-10 wt %, preferably 0.001-0.1 wt %, based on the weight of the aroma composition.

Addition of a compound of the formula (1) at such ratios to, for example, aroma compositions of fruits (e.g., strawberry, blueberry, raspberry, apple, cherry, plum, apricot, peach, pineapple, banana, melon, mango, papaia, kiwi fruit, pear, grape, muscat, "Kyoho" grape and the like); citrus fruits (e.g., lemon, orange, grapefruit, lime, mandarin and the like); Japanese citrus flavor (e.g., "mikan; *Citrus unshiu*", "kabosu; *Citrus sphaerocarpa*", "sudachi; *Citrus sudachi*", "hassaku; *Citrus hassaku*", "iyokan; *Citrus iyo*", "yuzu; *Citrus junos*", "shekwasha; *Citrus depressa*", kumquat and the like); and tea (e.g., black tea, oolong tea, green tea and the like) can impart and emphasize the flavor of fresh natural fruit to the aroma compositions. Also addition of a compound of the formula (1) at such ratios to perfume preparations of bergamot note, geranium note, rose note, bouquet note, hyacinth note, orchid note or floral note can enhance the characteristic fragrance of individual perfume and reproduce the fresh, natural note inherent in natural essential oil.

According to the invention, furthermore, food and beverage, perfumed cosmetics, hygienic, sanitary and medicinal products, which contain the compounds of the formula (1) as fragrance or flavor component can be offered, by blending those aroma compositions containing the compounds of the formula (1) as the active ingredient with those products.

Addition of a suitable amount of an aroma composition containing a compound of the formula (1) as the active ingredient to, for examples, beverages such as carbonated beverage, fruit juice beverage, fruit wine beverage, milk beverage, and the like; frozen deserts such as ice cream, sherbet, ice candy and the like; luxury foods such as Japanese style confection, Western style confection, chewing gum, bread, coffee, black tea, tea, tobacco and the like; soup such as Japanese style soup and Western style soup; processed meat products such as ham and sausage; seasoning, various instant foods and beverages, and various snacks, enables to offer such foods and beverages imparted with the unique aroma and flavor. Also addition of a suitable amount of an aroma composition containing a compound of the formula (1) as the active ingredient to, for example, shampoo, hair cream and other base preparations for hair; face powder, lipstick and other cosmetic bases or bases for toiletry washing powder or lotion can offer cosmetics perfumed with the unique fragrance. Furthermore, by blending a suitable amount of an aroma composition containing a compound of the formula (1) as the active ingredient with, for example, washing detergent, antiseptic detergent, deodorizing detergent and other hygienic and sanitary detergent; toothpaste, tissue paper, toilet paper, and the like; various hygienic sanitary materials, medicinal products and the like which are imparted with the unique fragrance can be offered.

EXAMPLES

Hereinafter the present invention is explained more specifically, referring to Examples.

Example 1

Following the series of the reaction formulae as presented below, 6,8,10-undecatrien-3-one of the formula (1-1) was synthesized. The percentages in the parentheses under the Step Nos. indicate the yield in each step.

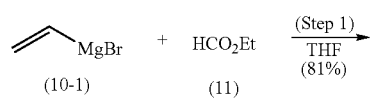

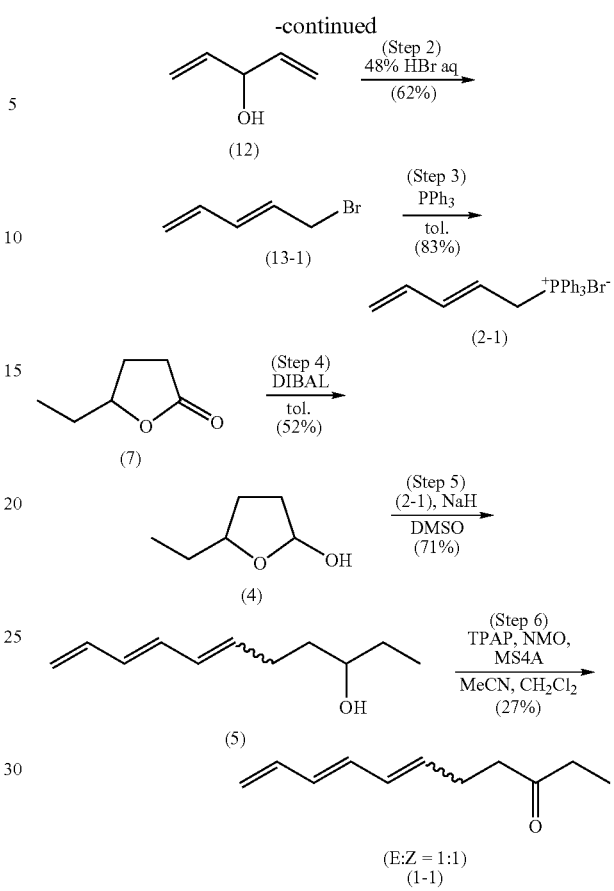

Step 1: Synthesis of the Alcohol (12)

In argon atmosphere, magnesium (48.6 g, 2.00 mol), tetrahydrofuran (300 mL) and iodine (cat.) were added to a 2 L flask, and while they were stirred at room temperature, a solution (ca. 20 mL) of vinyl bromide (214.0 g, 2.00 mol) in tetrahydrofuran (780 mL) was added dropwise. The reaction solution was heated to 30 to 40° C. to initiate the reaction, and the remainder of vinyl bromide in tetrahydrofuran was added dropwise over 1 h, so as to maintain the reaction temperature at 30 to 40° C. After completion of the dropping, the reaction solution mixture was stirred for 1.5 h at room temperature, followed by cooling with ice-water. Then ethyl formate (11) (74.0 g, 1.00 mol) was added dropwise over 1 h at 5 to 15° C., followed by stirring for 1 h at room temperature. The reaction solution was poured into saturated aqueous ammonium chloride solution (1 L), the organic layer was separated, and the aqueous layer was extracted with diethyl ether. All of the organic layers were combined and successively washed with saturated aqueous ammonium chloride solution and saturated aqueous sodium chloride solution. Then the organic layer was dried over magnesium sulfate, and concentrated under reduced pressure. The resulting residue (96.7 g) was distilled under reduced pressure (ca. 54° C./7.8 kPa) to give the alcohol (12) (68.2 g, 0.811 mol, yield 81%, purity 96%).

Step 2: Synthesis of Bromide (13-1)

The alcohol (12) (52.5 g, 0.625 mol) was added to a 300 mL flask, and 48% aqueous hydrogen bromide solution (126.2 g, 0.749 mol) was added dropwise over 1.5 h under cooling with ice-methanol. The organic layer was separated, washed with water and dried over magnesium sulfate to give the bromide (13-1) (57.1 g, 0.388 mol, yield 62%, purity 97%).

Step 3: Synthesis of the Phosphonium Salt (2-1)

Triphenylphosphine (106.8 g, 0.407 mol) and toluene (250 mL) were added to a 500 mL flask and the bromide (13-1) (57.1 g, 0.388 mol) was added dropwise over 15 min at room temperature. After stirring for 22 h at room temperature, the precipitated crystals were separated by filtration to give the phosphonium salt (2-1) (132.4 g, 0.323 mol, yield 83%).

Step 4: Synthesis of the Lactol (4)

In argon atmosphere, γ-hexylactone (7) (11.4 g, 100 mmol) and toluene (200 mL) were added to a 500 mL flask and diisobutylaluminum hydride (DIBAL) (1.01 M in toluene, 109 mL, 0.110 mol) was added dropwise over 30 min at −63 to −61° C. After completion of the dropping, the reaction mixture was stirred for 1 h at the temperature as it was, followed by addition of methanol (20 mL), Celite® and diethyl ether and stirring overnight at room temperature. The mixture was filtered, and the filtrate was concentrated under reduced pressure. The resulting residue (13.5 g) was distilled under reduced pressure (ca. 55° C./0.5 kPa) to give the lactol (4) (6.00 g, 51.7 mmol, yield 52%, purity 93%).

Step 5: Synthesis of 6,8,10-undecatrien-3-ol (5)

In argon atmosphere, dimethylsulfoxide (DMSO) (20 mL) was added to a 100 mL flask and sodium hydride (60% oil dispersion, 1.38 g, 34.4 mmol) was added at room temperature, followed by stirring for 1 h as it was. A solution of the phosphonium salt (2-1) (14.1 g, 34.4 mmol) in DMSO (10 mL) was added and stirred for 10 min at room temperature. Successively, a solution of the lactol (4) (2.00 g, 17.2 mmol) in DMSO (10 mL) was added at room temperature. After stirring overnight, the reaction solution was poured into water and extracted with diethyl ether. The organic layer was washed successively with water and saturated aqueous sodium chloride solution, dried over magnesium sulfate, filtered and concentrated under reduced pressure. To the residue diethyl ether was added, the precipitated crystals were separated by filtration, and the filtrate was concentrated under reduced pressure. Once again diethyl ether was added to the residue, the precipitated crystals were filtered off and the filtrate was concentrated under reduced pressure. The resulting residue was purified by silica gel column chromatography (hexane:ethyl acetate=30:1) to give 6,8,10-undecatrien-3-ol (5) (2.04 g, 12.3 mmol, yield 71%).

Step 6: Synthesis of 6,8,10-undecatrien-3-one (1-1)

In argon atmosphere, 6,8,10-undecatrien-3-ol (5) (1.80 g, 10.8 mmol), methylene chloride (45 mL), Molecular Sieves 4A (4.50 g), N-methylmorpholine N-oxide (NMO) (1.90 g, 16.2 mmol) and acetonitrile (5 mL) were added to a 100 mL flask, and further tetrapropylammonium perruthenate (TPAP) (190 mg, 0.541 mmol) was added, followed by stirring at room temperature for 4 h. TPAP (190 mg, 0.541 mmol) was added, followed by stirring for 2 h at room temperature. Then NMO (1.90 g, 16.2 mmol) was added, followed by stirring for 3 h at room temperature. Hexane was added to the reaction mixture which then was filtered, and the filtrate was concentrated under reduced pressure. Thus obtained residue was purified on silica gel column chromatography (hexane:ethyl acetate=50:1) to give 6,8,10-undecatrien-3-one (1-1) (476 mg, 2.90 mmol, yield 27%).

Example 2

Following the series of the reaction formulae as presented below, 6,8,10-undecatrien-3-one (1-1) was synthesized. The percentages in the parentheses under the Step Nos. indicate the yield in each step.

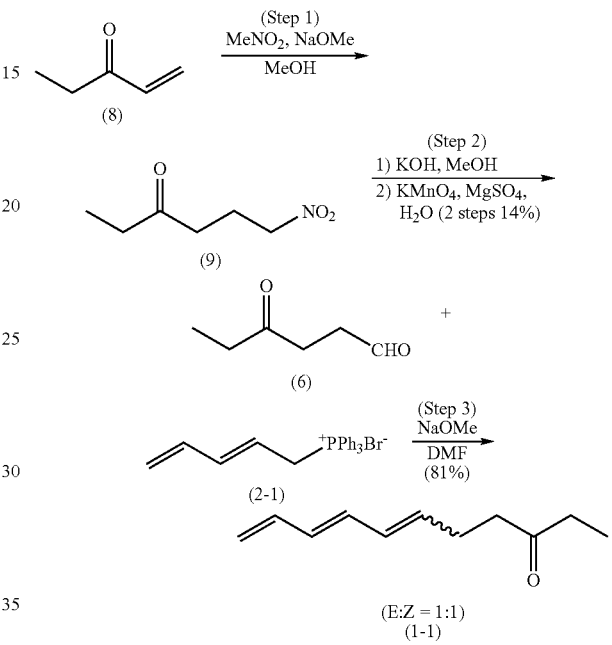

Step 1: Synthesis of the Nitro Compound (9)

Sodium methoxide (2.50 g, 46.3 mmol) and methanol (500 mL) were added to a 1 L flask, and into which a mixed solution of ethyl vinyl ketone (8) (23.2 g, 276 mmol) and nitromethane (100 g, 1.64 mol) was added under cooling with ice-water. After stirring for 0.5 h at the temperature as it was, the mixture was stirred at room temperature for 0.5 h. Acetic acid (2.8 g) was added to the reaction mixture, which then was concentrated under reduced pressure. Water was added to the residue which then was extracted with ethyl acetate. The organic layer was successively washed with saturated aqueous sodium hydrogencarbonate solution, water and saturated aqueous sodium chloride solution, dried over magnesium sulfate, filtered and concentrated under reduced pressure. The nitro compound (9) (33.5 g) obtained as the residue was used in the subsequent reaction as it was.

Step 2: Synthesis of the Ketoaldehyde (6)

The nitro compound (9) (25.6 g) and methanol (700 mL) were added to a 3 L flask, and to which a methanol solution (300 mL) of potassium hydroxide (15.0 g, 0.267 mol) was added dropwise over 10 min under cooling with dry ice-acetone. Maintaining the temperature as it was at the termination of the dropping, the reaction mixture was stirred for 20 minutes, and to which an aqueous solution (1 L) of potassium permanganate (23.7 g, 0.150 mol) and magnesium sulfate (20.0 g, 0.166 mol) was added dropwise over 1 h. After stirring for 1.5 h at the same temperature, the reaction mixture was concentrated under reduced pressure. Water was added to the residue which was then extracted with diethyl ether. The organic layer was washed successively with saturated aqueous sodium hydrogencarbonate solution and saturated aqueous sodium chloride solution, dried over magnesium sulfate, filtered, and concentrated under reduced pressure. The resulting residue (9.23 g) was distilled under reduced pressure (ca. 58° C./0.67 kPa) to give the ketoaldehyde (6) (3.20 g, 28.0 mmol, yield 14%).

Step 3: Synthesis of 6,8,10-undecatrien-3-one (1-1)

In nitrogen atmosphere, ketoaldehyde (6) (1.00 g, 8.76 mmol), phosphonium salt (2-1) (3.60 g, 8.78 mmol) and N,N-dimethylformamide (DMF) (10 mL) were added to a 30 mL flask, and into which sodium methoxide (28% methanol solution) (1.72 g, 8.92 mmol) was added dropwise under cooling with ice-water, followed by stirring for 1 h. The reaction mixture was poured into saturated aqueous ammonium chloride solution and extracted with hexane. The organic layer was washed successively with water and saturated aqueous sodium chloride solution, dried over magnesium sulfate, filtered and concentrated under reduced pressure. The resulting residue (1.92 g) was purified by silica gel column chromatography (hexane: ethyl acetate=100:1) to give 6,8,10-undecatrien-3-one (1-1) (1.16 g, 7.06 mmol, yield 81%).

Properties of 6,8,10-undecatrien-3-one (1-1)

Ratio of the geometrical isomers at 6-position: E:Z=1:1

$^1$H-NMR (mixture of geometrical isomers at 6-position, CDCl$_3$, 400 MHz): δ 1.04 (3H, t, J=7.3), 2.41 (2H, q, J=7.3), 2.34-2.51 (4H, m), 5.04, 5.08 (total 1H dd, d, J=1.4, 9.6, J=10.1), 5.16, 5.20 (total 1H, each d, J=16.9, J=17.0), 5.40, 5.68 (total 1H, each dt, J=6.8, 11.0, J=7.3, 14.6), 5.98-6.52 (4H, m).

$^{13}$C-NMR (mixture of geometrical isomers at 6-position, CDCl$_3$, 100 MHz): δ 7.8, 22.3, 27.0, 36.0, 41.7, 42.0, 116.7, 117.4, 128.1, 129.2, 130.9, 131.0, 131.7, 133.0, 133.6, 133.7, 137.0, 137.1, 210.6, 210.7.

MS (m/z): 29(24), 41(13), 57(100), 65(10), 77(29), 91(40), 107(13), 117(6), 135(2), 164 (M$^+$, 22)

Example 3

Odor Evaluation

An odor evaluation test was given by well trained panelists, to 0.1% ethanol solutions of each of the 6,8,10-undecatrien-3-one as obtained in Example 1, 1,3,5-undecatriene and 1,3,5,7-undecatetraene as described in JP 50(1975)-32105A and JP 59(1984)-42326A, respectively. The odor evaluation was performed with 30-mL sample phials each containing the 0.1% ethanol solution of each compound, and the odor at each phial mouth and that of scent paper applied with each of the solutions were examined. Five panelists' average odor evaluations are shown in Table 1.

TABLE 1

Odor Evaluation

| Compound | Odor Evaluation |
| --- | --- |
| 6,8,10-undecatrien-3-one | sweet, fruity note rich in naturality and freshness in addition to green note with dry woody tone |
| 1,3,5-undecatriene | floral note including fresh leafy tone |
| 1,3,5,7-undecatetraene | woody and earthy note reminiscent of leaves and flowers |

Example 4

As a pineapple-flavored, formulated aroma composition, a basic aroma composition formed of the components as shown in the following Table 2 was prepared.

TABLE 2

A Pineapple-flavored, Basic Formulated Aroma Composition

| Blended Component | Blended Amount (g) |
| --- | --- |
| ethyl acetate | 300 |
| ethyl butyrate | 250 |
| isoamyl acetate | 100 |
| isoamyl valerate | 55 |
| isobutyric acid | 70 |
| isovaleric acid | 30 |
| allyl caproate | 35 |
| ethyl caproate | 20 |
| ethyl caprylate | 15 |
| ethyl caprate | 20 |
| isoamyl alcohol | 35 |
| diethyl malonate | 30 |
| citral | 15 |
| Linalool | 5 |
| Maltol | 20 |
| Total | 1000 |

A novel pineapple-flavored, formulated aroma composition was prepared by adding 0.1 g of the 6,8,10-undecatrien-3-one as prepared in Example 1 to 99.9 g of the above composition. Aroma of the novel pineapple-flavored composition and that of the composition as prepared in the above to which the compound was not added, were compared by ten expert panelists. In consequence, all of the ten expert panelists evaluated the novel formulated aroma composition to which the compound was added, as well reproducing the characteristic odor of natural pineapple with emphasized fresh, natural fruity note and being excellent also in lasting effect.

Example 5

As a hyacinth-scented formulated composition, a basic aroma composition formed of the components as shown in the following Table 3 was prepared.

TABLE 3

A Hyacinth-scented, Basic Formulated Aroma Composition

| Blended Component | Blended Amount (g) |
| --- | --- |
| Phenylacetaldehyde | 100 |
| cinnamic alcohol | 150 |
| hyacinth absolute | 20 |
| phenylethyl alcohol | 100 |
| α-ionone | 30 |

TABLE 3-continued

A Hyacinth-scented, Basic Formulated Aroma Composition

| Blended Component | Blended Amount (g) |
|---|---|
| benzyl propionate | 70 |
| ylang-ylang oil | 20 |
| amylcinnamic aldehyde | 50 |
| Isoeugenol | 40 |
| benzyl alcohol | 100 |
| dimethylbenzyl carbinol | 30 |
| galbanum resinoid | 50 |
| phenylacetaldehyde dimethyl acetal | 80 |
| lauryl alcohol | 20 |
| Nerol | 80 |
| Heliotropine | 60 |
| Total | 1000 |

A novel hyacinth-scented formulated aroma composition was prepared by adding 0.1 g of the 6,8,10-undecatrien-3-one as prepared in Example 1 to 99.9 g of the above composition. Aroma of the novel formulated aroma composition and that of the hyacinth-scented aroma composition as prepared in the above to which the compound was not added, were compared by ten expert panelists. In consequence, all of the ten expert panelists evaluated the novel formulated aroma composition to which the compound was added, as well reproducing the characteristic odor of natural hyacinth with emphasized fresh and natural note and being excellent also in lasting effect.

Example 6

Odor Evaluation of 6E Form and 6Z Form

In relation to the 6,8,10-undecatrien-3-one as obtained in Example 1 in which the ratio of the geometrical isomers at 6-position, E:Z=1:1, odors of (6E,8E)-6,8,10-undecatrien-3-one and (6Z,8E)-6,8,10-undecatrien-3-one were evaluated by gas chromatography-olfactometry.

Odor Evaluation (6E,8E)-6,8,10-undecatrien-3-one: mild green note and sweet fruity note rich in naturality and freshness.

(6Z,8E)-6,8,10-undecatrien-3-one: woody green note and sharp, sweet fruity note rich in naturality and freshness.

Example 7

Following the series of the reaction formulae as presented below, 6,8,10-undecatrien-4-one of the formula (1-2) was synthesized. The percentages in the parentheses under the Step Nos. indicate the yield in each step.

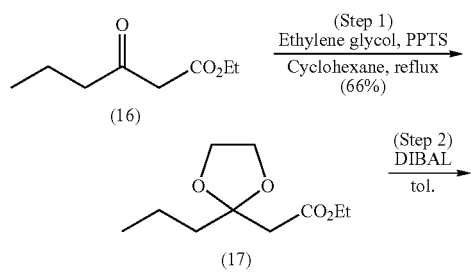

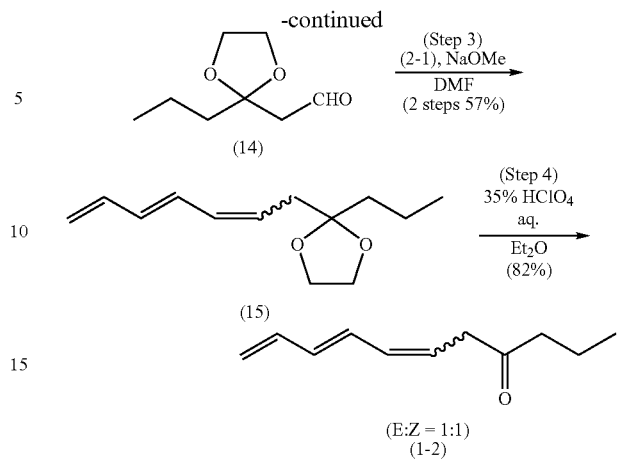

Step 1: Synthesis of the Ester (17)

Ethyl 3-oxohexanoate (16) (12.0 g, 78.9 mmol), ethylene glycol (9.40 g, 151 mmol), pyridinium p-toluenesulfonate (PPTS) (0.1 g) and cyclohexane (50 mL) were added to a 200 mL flask, and the mixture was refluxed for 9 h while removing the generated water. Then p-toluenesulfonic acid (TsOH) (cat.) was added, followed by refluxing for 6 h, while removing the generated water. After cooling, saturated aqueous sodium hydrogencarbonate solution was added to the reaction mixture and the organic layer was separated. The organic layer was successively washed with water and saturated aqueous sodium chloride solution, dried over magnesium sulfate, and evaporated under reduced pressure. The resulting residue (14.9 g) was distilled under reduced pressure (ca. 77° C./0.2 kPa) to give the ester (17) (10.6 g, 52.4 mmol, yield 66%).

Step 2: Synthesis of the Aldehyde (14)

In argon atmosphere, the ester (17) (5.00 g, 24.7 mmol) and toluene (50 mL) were added to a 200 mL flask and diisobutylaluminum hydride (DIBAL) (0.99 M in toluene, 24.9 mL, 24.7 mmol) was added dropwise over 30 min while stirring at −65 to −60° C., followed by stirring for 30 min at the temperature as it was. The reaction mixture was poured into 5% aqueous oxalic acid dehydrate solution (140 mL), the organic layer was separated, and the aqueous layer was extracted with ethyl acetate. All of the organic layers were combined and washed with saturated aqueous sodium chloride solution. Then the organic layer was dried over magnesium sulfate, and evaporated under reduced pressure. The resulting residue (the aldehyde (14), 4.20 g) was used in the next step as it was.

Step 3: Synthesis of the Trieneacetal (15)

In nitrogen atmosphere, the aldehyde (14) (4.20 g), the phosphonium salt (2-1) which was obtained in Step 3 of Example 1 (10.1 g, 27.2 mmol) and dimethylformamide (DMF) (16 g) were added to a 200 mL flask and sodium methoxide (28% in methanol, 5.00 g, 25.9 mmol) was added dropwise while cooling with ice-water (5-10° C.), followed by stirring for 1 h at the temperature as it was. The reaction mixture was poured into saturated aqueous ammonium chloride solution, to which hexane was added, and the precipitated crystals were separated by filtration. The filtrate was extracted with hexane and washed successively with water and saturated aqueous sodium chloride solution, dried over magnesium sulfate and evaporated under reduced pressure. The resulting residue (5.92 g) was distilled under reduced pressure (ca. 100° C./0.2 kPa) to give the trieneacetal (15) (2.94 g, 14.1 mmol, yield 57%).

Step 4: Synthesis of 6,8,10-undecatrien-4-one (1-2)

Thirty-five (35) % aqueous perchloric acid solution (40 mL) and diethyl ether (10 mL) were added to a 200 mL flask and a solution of the trieneacetal (15) (2.94 g, 0.014 mol) in diethyl ether (30 mL) was added dropwise over 10 min while cooling with ice-water (5-10° C.), followed by stirring for 20 min at the temperature as it was. The reaction mixture was neutralized to pH 7-8 with saturated aqueous sodium hydrogencarbonate solution and extracted with diethyl ether. The organic layer was washed successively with water and saturated aqueous sodium chloride solution, dried over magnesium sulfate, and evaporated under reduced pressure. The resulting residue (2.61 g) was purified by silica gel column chromatography (hexane:ethyl acetate=80:1) to give 6,8,10-undecatrien-4-one (1-2) (1.90 g, 11.6 mmol, yield 82%).

Properties of 6,8,10-undecatrien-4-one (1-2)

Ratio of the geometrical isomers at 6-position: E:Z=1:1
$^1$H-NMR (mixture of geometrical isomers at 6-position, $CDCl_3$, 400 MHz): δ 0.89, 0.90 (total 3H, each t, J=7.2, J=7.2), 1.55-1.64 (2H, m), 2.40, 2.42 (total 2H, each t, J=6.8, J=7.6), 3.18 (1H, d, J=7.2), 3.29 (1H, d, J=7.2), 5.07, 5.12 (total 1H, each d, J=10.0, J=10.4), 5.20, 5.24 (total 1H, each d, J=18.4, J=18.0), 5.62, 5.78 (total 1H, each dt, J=7.6, 10.8, J=7.2, 15.2), 6.08-6.43 (4H, m).
$^{13}$C-NMR (mixture of geometrical isomers at 6-position, $CDCl_3$, 100 MHz): δ13.7, 17.1, 17.2, 42.1, 44.3, 46.8, 117.4, 118.2, 123.3, 126.2, 127.5, 131.2, 132.5, 132.8, 133.7, 134.8, 136.8, 208.1, 208.6.
MS (m/z): 41(21), 43(100), 71(99), 77(25), 91(25), 164 ($M^+$, 18)

Example 8

Odor Evaluation

An odor evaluation test was given by well trained panelists, to 0.1% ethanol solutions of each of the 6,8,10-undecatrien-4-one as obtained in Example 7, 1,3,5-undecatriene and 1,3,5,7-undecatetraene as described in JP 50(1975)-32105A and JP 59(1984)-42326A, respectively. The odor evaluation was performed with 30-mL sample phials each containing the 0.1% ethanol solution of each compound, and the odor at each phial mouth and that of scent paper applied with each of the solutions were examined. Five panelists' average odor evaluations are shown in Table 4.

TABLE 4

| Odor Evaluation | |
|---|---|
| Compound | Odor Evaluation |
| 6,8,10-undecatrien-4-one | sweet, fruity note rich in naturality and freshness in addition to green note with dry woody tone |
| 1,3,5-undecatriene | floral note including fresh leafy tone |
| 1,3,5,7-undecatetraene | woody and earthy note reminiscent of leaves and flowers |

Example 9

As a pineapple-flavored, formulated aroma composition, a basic aroma composition formed of the components as shown in the following Table 5 was prepared.

TABLE 5

| A Pineapple-flavored, Basic Formulated Aroma Composition | |
|---|---|
| Blended Component | Blended Amount (g) |
| ethyl acetate | 300 |
| ethyl butyrate | 250 |
| isoamyl acetate | 100 |
| isoamyl valerate | 55 |
| isobutyric acid | 70 |
| isovaleric acid | 30 |
| allyl caproate | 35 |
| ethyl caproate | 20 |
| ethyl caprylate | 15 |
| ethyl caprate | 20 |
| isoamyl alcohol | 35 |
| diethyl malonate | 30 |
| citral | 15 |
| linalool | 5 |
| maltol | 20 |
| Total | 1000 |

A novel pineapple-flavored, formulated aroma composition was prepared by adding 0.1 g of the 6,8,10-undecatrien-4-one as prepared in Example 7 to 99.9 g of the above composition. Aroma of the novel pineapple-flavored composition and that of the composition as prepared in the above to which the compound was not added, were compared by ten expert panelists. In consequence, all of the ten expert panelists evaluated the novel formulated aroma composition to which the compound was added, as well reproducing the characteristic odor of natural pineapple with emphasized fresh, natural fruity note and being excellent also in lasting effect.

Example 10

As a hyacinth-scented formulated composition, a basic aroma composition formed of the components as shown in the following Table 6 was prepared.

TABLE 6

| A Hyacinth-Scented, Basic Formulated Aroma Composition | |
|---|---|
| Blended Component | Blended Amount (g) |
| Phenylacetaldehyde | 100 |
| cinnamic alcohol | 150 |
| hyacinth absolute | 20 |
| phenylethyl alcohol | 100 |
| α-ionone | 30 |
| Benzyl propionate | 70 |
| ylang-ylang oil | 20 |
| amylcinnamic aldehyde | 50 |
| Isoeugenol | 40 |
| benzyl alcohol | 100 |
| dimethylbenzyl carbinol | 30 |
| galbanum resinoid | 50 |
| phenylacetaldehyde dimethyl acetal | 80 |
| lauryl alcohol | 20 |
| Nerol | 80 |
| Heliotropine | 60 |
| Total | 1000 |

A novel hyacinth-scented formulated aroma composition was prepared by adding 0.1 g of the 6,8,10-undecatrien-4-one as prepared in Example 7 to 99.9 g of the above composition. Aroma of the novel formulated aroma composition and that of the hyacinth-scented aroma composition as prepared in the above to which the compound was not added, were compared by ten expert panelists. In consequence, all of the ten expert panelists evaluated the novel formulated aroma composition to which the compound was added, as well reproducing the characteristic odor of natural hyacinth with emphasized fresh and natural note and being excellent also in lasting effect.

Example 11

Odor Evaluation of 6E Form and 6Z Form

In relation to the 6,8,10-undecatrien-4-one as obtained in Example 7 in which the ratio of the geometrical isomers at 6-position, E:Z=1:1, odors of (6E,8E)-6,8,10-undecatrien-4-one and (6Z,8E)-6,8,10-undecatrien-4-one were evaluated by gas chromatography-olfactometry.

Aroma Evaluation (6E,8E)-6,8,10-undecatrien-4-one: mild green note and sweet fruity note rich in naturality and freshness.

(6Z,8E)-6,8,10-undecatrien-4-one: woody green note and sharp, sweet fruity note rich in naturality and freshness.

The invention claimed is:

1. 6,8,10-Undecatrien-3-one or 6,8,10-undecatrien-4-one, which are represented by the following formula (1):

(1)

[in the formula, either one of A and B stands for carbonyl group, and the other stands for methylene group, the wavy line signifying cis-form, trans-form or a mixture of cis- and trans-forms at an optional ratio].

2. An aroma composition which is characterized by containing 6,8,10-undecatrien-3- or -4-one of the formula (1) in claim 1 as the active ingredient.

3. A product characterized by containing the aroma composition of claim 2.

4. A method of producing 6,8,10-undecatrien-3-one which is represented by the following formula (1-1)

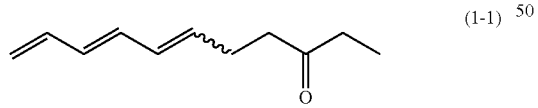

(1-1)

[in the formula, the wavy line signifies cis-form, trans-form or a mixture of cis- and trans-forms at an optional ratio] which is characterized by comprising subjecting a phosphonium salt represented by the following formula (2)

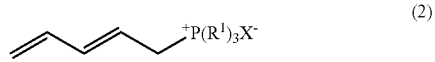

(2)

[in the formula, $R^1$ stands for an aryl and X stands for a halogen]

or a phosphonate of the following formula (3)

(3)

[in the formula, $R^2$ stands for a $C_{1-8}$ alkyl or aryl]

to Wittig reaction or Horner-Emmons reaction, with a lactol of the following formula (4)

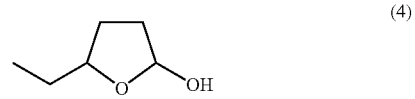

(4)

and oxidizing the resulting 6,8,10-undecatrien-3-ol of the following formula (5)

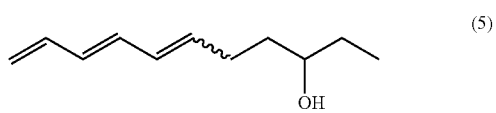

(5)

[in the formula, the wavy line signifies cis-form, trans-form or a mixture of cis- and trans-forms at an optional ratio].

5. A method for producing 6,8,10-undecatrien-3-one which is represented by the following formula (1-1)

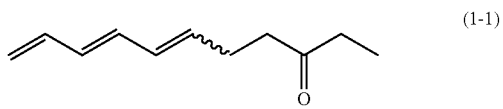

(1-1)

[in the formula, the wavy line signifies cis-form, trans-form, or a mixture of cis- and trans-forms at an optional ratio]

which is characterized by comprising subjecting a phosphonium salt of the following formula (2)

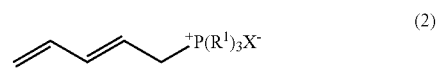

(2)

[in the formula, $R^1$ stands for an aryl and X stands for a halogen]

or a phosphonate of the following formula (3)

(3)

[in the formula, $R^2$ stands for a $C_{1-8}$ alkyl or aryl]

to Wittig reaction or Horner-Emmons reaction, with a ketoaldehyde of the following formula (6)

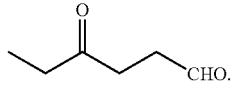
(6)

6. A method for producing 6,8,10-undecatrien-4-one which is represented by the following formula (1-2)

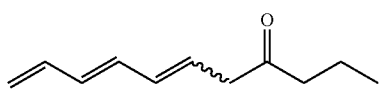
(1-2)

[in the formula, the wavy line signifies cis-form, trans-form, or a mixture of cis- and trans-forms at an optional ratio]
which is characterized by comprising subjecting a phosphonium salt represented by the following formula (2)

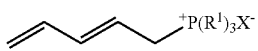
(2)

[in the formula, $R^1$ stands for an aryl and X stands for a halogen]

or a phosphonate of the following formula (3)

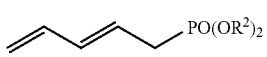
(3)

[in the formula, $R^2$ stands for a $C_{1-8}$ alkyl or aryl]
to Wittig reaction or Horner-Emmons reaction, with an aldehyde of the following formula (14)

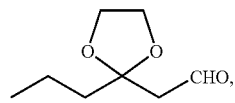
(14)

and deacetalizing the resulting trieneacetal of the following formula (15)

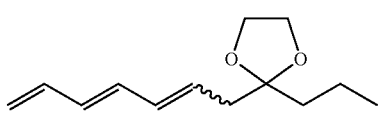
(15)

[in the formula, the wavy line signifies cis-form, trans-form or a mixture of cis- and trans-forms at an optional ratio].

* * * * *